United States Patent
Choi et al.

(10) Patent No.: US 9,925,525 B2
(45) Date of Patent: Mar. 27, 2018

(54) BISMUTH MOLYBDATE-BASED CATALYST HAVING ZEOLITE COATING LAYER, METHOD OF PREPARING THE SAME, AND METHOD OF PREPARING 1,3-BUTADIENE USING THE SAME

(71) Applicant: LG CHEM, LTD., Seoul (KR)

(72) Inventors: Dae Heung Choi, Daejeon (KR); Dong Hyun Ko, Daejeon (KR); Jun Han Kang, Daejeon (KR); Kyong Yong Cha, Daejeon (KR); Dae Chul Kim, Daejeon (KR); Joo Hyuck Lee, Daejeon (KR); Hyun Seok Nam, Daejeon (KR); Myung Ji Suh, Daejeon (KR); Ye Seul Hwang, Daejeon (KR); Jun Kyu Han, Daejeon (KR); Sang Jin Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 342 days.

(21) Appl. No.: 14/427,207

(22) PCT Filed: Nov. 18, 2014

(86) PCT No.: PCT/KR2014/011087
§ 371 (c)(1),
(2) Date: Mar. 10, 2015

(87) PCT Pub. No.: WO2015/072820
PCT Pub. Date: May 21, 2015

(65) Prior Publication Data
US 2016/0256855 A1    Sep. 8, 2016

(30) Foreign Application Priority Data

Nov. 18, 2013  (KR) .................. 10-2013-0139970
Nov. 18, 2014  (KR) .................. 10-2014-0160918

(51) Int. Cl.
*B01J 23/887*    (2006.01)
*C07C 5/48*    (2006.01)
(Continued)

(52) U.S. Cl.
CPC ......... *B01J 23/8876* (2013.01); *B01J 23/002* (2013.01); *B01J 23/31* (2013.01);
(Continued)

(58) Field of Classification Search
CPC .................................................. B01J 23/8876
See application file for complete search history.

(56) References Cited

U.S. PATENT DOCUMENTS

| | | | | |
|---|---|---|---|---|
| 4,148,757 A | * | 4/1979 | Brazdil | B01J 23/002 502/204 |
| 4,677,084 A | * | 6/1987 | Bergna | B01J 23/002 502/214 |

(Continued)

FOREIGN PATENT DOCUMENTS

| | | |
|---|---|---|
| CN | 103298771 A | 9/2013 |
| JP | H04-5245 A | 1/1992 |

(Continued)

OTHER PUBLICATIONS

Khan, Easir A. et al., Preparation of metal oxide/zeolite core-shell nanostructures, Microporous and Mesoporous Materials 118: 210-217 (2009).

(Continued)

*Primary Examiner* — Douglas B Call
(74) *Attorney, Agent, or Firm* — Dentons US LLP

(57) ABSTRACT

The present invention relates to a bismuth molybdate-based composite oxide catalyst having a microporous zeolite coating layer on the surface thereof and thus having high selectivity for 1,3-butadiene, a method of preparing the same, and a method of preparing 1,3-butadiene using the
(Continued)

same. The catalyst has a microporous zeolite coating layer, and thus enables only gaseous products (light) to selectively pass through the zeolite coating layer, improving selectivity for 1,3-butadiene.

13 Claims, 3 Drawing Sheets

(51) Int. Cl.
*B01J 37/02* (2006.01)
*B01J 29/04* (2006.01)
*B01J 35/02* (2006.01)
*B01J 23/31* (2006.01)
*B01J 23/00* (2006.01)
*B01J 29/076* (2006.01)
*B01J 29/26* (2006.01)
*B01J 29/48* (2006.01)
*B01J 29/78* (2006.01)

(52) U.S. Cl.
CPC ............ *B01J 29/04* (2013.01); *B01J 29/076* (2013.01); *B01J 35/026* (2013.01); *B01J 37/0221* (2013.01); *B01J 37/0236* (2013.01); *B01J 37/0246* (2013.01); *C07C 5/48* (2013.01); *B01J 29/26* (2013.01); *B01J 29/48* (2013.01); *B01J 29/7807* (2013.01); *B01J 29/7815* (2013.01); *B01J 2229/64* (2013.01); *B01J 2523/00* (2013.01); *C07C 2523/04* (2013.01); *C07C 2523/28* (2013.01); *C07C 2523/31* (2013.01); *C07C 2523/745* (2013.01); *C07C 2523/75* (2013.01); *C07C 2523/887* (2013.01)

(56) References Cited

U.S. PATENT DOCUMENTS

| | | | |
|---|---|---|---|
| 5,550,309 | A | 8/1996 | Maunders et al. |
| 6,924,387 | B1 | 8/2005 | Chang et al. |
| 6,936,561 | B2 * | 8/2005 | Marques ............... B01D 53/885 502/60 |
| 2003/0092565 | A1 * | 5/2003 | Chaudhari ............. B01J 27/188 502/150 |
| 2005/0032628 | A1 | 2/2005 | Collier et al. |
| 2006/0011514 | A1 * | 1/2006 | van den Berge ........ B01J 29/80 208/120.01 |
| 2009/0036294 | A1 | 2/2009 | Bouizi et al. |
| 2009/0088594 | A1 | 4/2009 | Oh et al. |
| 2010/0249482 | A1 | 9/2010 | Chung et al. |
| 2013/0281748 | A1 | 10/2013 | Cha et al. |
| 2016/0045900 | A1 * | 2/2016 | Walzel ................ B01J 37/0009 568/448 |

FOREIGN PATENT DOCUMENTS

| | | | | |
|---|---|---|---|---|
| JP | | H045245 A | * 1/1992 | ............. B01J 23/88 |
| JP | | H0455245 A | 1/1992 | |
| JP | | H08-501094 A | 2/1996 | |
| JP | | 2007519518 A | 7/2007 | |
| JP | | 2012046509 A | 3/2012 | |
| JP | | 2013043125 A | 3/2013 | |
| JP | | 2013100244 A | 5/2013 | |
| KR | 10-2000-0007459 A | | 2/2000 | |
| KR | 10-2007-0103219 A | | 10/2007 | |
| KR | | 10-0888133 B1 | 3/2009 | |
| KR | 10-2011-0130130 A | | 12/2011 | |
| KR | 10-2013-0046214 A | | 5/2013 | |
| WO | | 03033625 A2 | 4/2003 | |
| WO | | 2013002459 A1 | 1/2013 | |
| WO | WO 2014/147187 | | * 9/2014 | |

OTHER PUBLICATIONS

Nishiyama, Norikazu et al., Zeolite membrane on catalyst particles for selective formation of p-xylene in the disproportionation of toluene, Chemcomm Communication 1746-1747 (2001).

Zhang, Xiongfu et al., Influence of seed size on the formation and microstructure of zeolite silicalite-1 membranes by seeded growth, Materials Chemistry and Physics 96: 42-50 (2006).

XP-0027625, P-xylene production comprises catalytically reacting isobutylene with molecular oxygen in presence of catalyst and silica-alumina or zeolite carrier, citing JP19900107882 (Watanabe et al.), published Apr. 24, 1990. Corresponding to Foreign Patent Document #1.

Database, WPI, Week 199208; Thomson Scientific, London, GB; AN 1992-060699 XP-002762591, citing JP19900107882 (Watanabe et al.), previously made of record.

Mabande et al., "A study of Silicalite-1 and A1-ZSM-5 membrane synthesis on stainless steel supports," Microporous and Mesoporous Materials 75: 209-220 (2004).

Hiroo Tominaga, "Science and Application of Zeolite," Kodansha Scientific, Tokyo, Japan (1987) pp. 130-132 [partial English translation].

Kong Chun-long et al., "Synthesis of Silicalite-1 Zeolite Membrane by Nanocrystal Seed Coating Method," The Chinese Journal of Process Engineering 7(1): 71-74 (2007) [Abstract].

* cited by examiner

BISMUTH MOLYBDATE-BASED CATALYST HAVING ZEOLITE COATING LAYER, METHOD OF PREPARING THE SAME, AND METHOD OF PREPARING 1,3-BUTADIENE USING THE SAME

This application is a National Stage Entry of International Application No. PCT/KR2014/011087, filed Nov. 18, 2014, and claims the benefit of Korean Application No. 10-2013-0139970, filed on Nov. 18, 2013, and Korean Application No. 10-2014-0160918, filed Nov. 18, 2014, all of which are hereby incorporated by reference in their entirety for all purposes as if fully set forth herein.

TECHNICAL FIELD

The present invention relates to a bismuth molybdate-based composite oxide catalyst having a microporous zeolite coating layer on the surface thereof and thus having high selectivity for 1,3-butadiene, a method of preparing the same, and a method of preparing 1,3-butadiene using the same.

BACKGROUND ART 1,3-butadiene is an intermediate product of petroleum chemicals in a petrochemical market, and demands for 1,3-butadiene and its value are gradually increasing. Naphtha cracking, direct dehydrogenation of n-butene, and oxidative dehydrogenation of n-butene are known as a method of preparing such 1,3-butadiene. However, the naphtha cracking process which occupies 90% or more of 1,3-butadiene supplied to the market has shortcomings in that energy consumption is high due to a high reaction temperature and also other fractions in addition to 1,3-butadiene are redundantly produced because the naphtha cracking process is not an exclusive process only for the production of 1,3-butadiene. Furthermore, the direct dehydrogenation of n-butene is not suitable for a commercial process for the production of 1,3-butadiene because it is not only thermodynamically unfavorable but also endothermic and thus requires high-temperature and low-pressure conditions to produce 1,3-butadiene with high yield.

The oxidative dehydrogenation (ODH) of n-butene which produces butadiene through oxidative dehydrogenation of n-butene produces 1,3-butadiene by removing two hydrogen atoms from n-butene using oxygen as a reactant so that stable water is produced as a product. Thus, the ODH is very advantageous thermodynamically, and is exothermic contrary to the direct dehydrogenation, so that 1,3-butadiene can be obtained with high yield even at a low temperature compared with the direct dehydrogenation. Therefore, a process of producing 1,3-butadiene through the oxidative dehydrogenation of n-butene may be an effective and exclusive production process satisfying increasing demands for 1,3-butadiene. Therefore, studies on a method of producing 1,3-butadiene having high selectivity by improving efficiency through the oxidative dehydrogenation of n-butene are being carried out.

Under the aforementioned background, while studying a bismuth molybdate-based composite oxide catalyst having high selectivity for 1,3-butadiene, the present inventors completed the present invention by finding that a catalyst having a microporous zeolite coating layer on the surface thereof not only enables products to selectively pass through the zeolite coating layer to thereby have high selectivity for 1,3-butadiene, but also simplifies phases of products by discharging solid organic by-products as a gas phase, which makes it easy to perform a purification process on products.

DISCLOSURE OF THE INVENTION

Technical Problem

It is an object of the present invention to provide a bismuth molybdate-based composite oxide catalyst having a microporous zeolite coating layer on the surface thereof and thus having high selectivity for 1,3-butadiene.

It is another object of the present invention to provide a method of preparing the bismuth molybdate-based composite oxide catalyst having a zeolite coating layer on the surface thereof.

It is still another object of the present invention to provide a method of preparing 1,3-butadiene with high yield through oxidative dehydrogenation of butene, using the bismuth molybdate-based composite oxide catalyst having a zeolite coating layer on the surface thereof.

Technical Solution

According to an embodiment of the present invention, a bismuth molybdate-based composite oxide catalyst for preparing 1,3-butadiene includes: a bismuth molybdate-based composite oxide expressed by Formula 1 below; a zeolite coating layer having micropores and formed on the surface of the bismuth molybdate-based composite oxide.

$$Mo_aBi_bFe_cCo_dE_eO_y \qquad \text{[Formula 1]}$$

where, E is at least one selected from the group consisting of nickel, sodium, potassium, rubidium, and cesium; the a, b, c, d and e each is 0.001 to 1; and the y is a value determined to adjust a valence by other element.

Also, according to another embodiment of the present invention, a method of preparing a bismuth molybdate-based composite oxide catalyst having a zeolite coating layer on the surface thereof includes: preparing a bismuth molybdate-based composite oxide expressed by Formula 1 (step 1); dipping the prepared bismuth molybdate-based composite oxide into a zeolite seed solution and leaving the bismuth molybdate-based composite oxide as it is, then drying and firing the bismuth molybdate-based composite oxide to form zeolite seeds on the surface of the bismuth molybdate composite oxide (step 2); and impregnating, into a zeolite synthesizing solution, the bismuth molybdate composite oxide with the zeolite seeds formed, and then drying the bismuth molybdate composite oxide (step 3).

Furthermore, according to still another embodiment of the present invention, a method of preparing 1,3-butadiene includes: filling a reactor with the bismuth molybdate-based composite oxide catalyst having a zeolite coating layer on the surface thereof as a fixed bed (step A); and performing oxidative dehydrogenation while continuously passing reactants containing C4 compounds including n-butene through a catalyst layer of the reactor filled with the catalyst (step B).

Advantageous Effects

A bismuth molybdate-based composite oxide catalyst having a zeolite coating layer on the surface thereof for preparing 1,3-butadiene according to the present invention has a microporous zeolite coating layer, thus enables gaseous products (light) including 1,3-butadiene as a target product to selectively pass through the zeolite coating layer, and therefore has high selectivity for 1,3-butadiene.

Also, the bismuth molybdate-based composite oxide catalyst can prevent a blockade of pipe line caused by solid organic by-products and simplify a separation process because solid organic by-products cannot pass through the catalyst due to the zeolite coating layer but adheres to the surface of the catalyst, and the adhered solid organic by-products may be discharged in the form of $CO_x$ gas such as carbon dioxide by continuously supplied oxygen.

Moreover, a method of preparing the bismuth molybdate-based composite oxide catalyst having a zeolite coating layer according to the present invention includes forming a zeolite seed layer on the surface of a bismuth molybdate-based composite oxide, and then allowing zeolite to grow around the seed to form a zeolite coating layer. Thus, the method enables homogeneous synthesis of a zeolite coating layer on the surface of the catalytic core layer without any separation between the catalytic core layer (bismuth molybdate-based composite oxide) and the zeolite coating layer.

Therefore, the bismuth molybdate-based composite oxide catalyst having a zeolite coating layer and the method of preparing the same according to the present invention may be easily applied to industry in need thereof, and particularly to catalyst manufacturing industries and 1,3-butadiene manufacturing industries.

BRIEF DESCRIPTION OF THE DRAWINGS

The accompanying drawings herein illustrate exemplary embodiments of the present invention and, together with the description, serve to provide a further understanding of the inventive concept, and thus the present invention should not be construed as being limited to only the drawings.

FIG. 3 shows results obtained from morphology analysis of a bismuth molybdate-based composite oxide catalyst having a zeolite coating layer according to an embodiment of the present invention, wherein

FIG. 4 shows results obtained from morphology analysis of a bismuth molybdate-based composite oxide catalyst without a zeolite coating layer according to an embodiment of the present invention, wherein

DESCRIPTIONS OF THE REFERENCE NUMERALS

Figure 1:
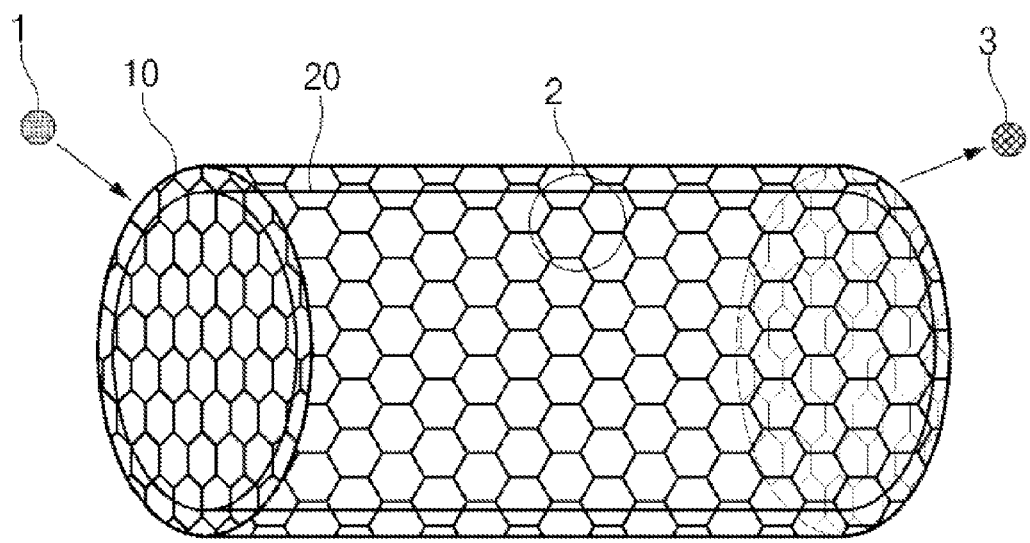
FIG. 1 schematically illustrates catalysis of a bismuth molybdate-based composite oxide catalyst having a zeolite coating layer according to an embodiment of the present invention.

10: zeolite coating layer
20: bismuth molybdate-based composite oxide
1: reactant
2: organic by-product
3: product
①: bismuth molybdate-based composite oxide
②: zeolite seed solution
③: drying and firing
④: zeolite synthesizing solution
⑤: bismuth molybdate-based composite oxide catalyst having zeolite coating layer on the surface thereof.

MODE FOR CARRYING OUT THE INVENTION

Hereinafter, the present invention will be described in more detail to help understanding the present invention.

Terms or words used in the description and claims should not be restrictively interpreted as ordinary or dictionary meanings, but should be interpreted as meanings and concepts conforming to the inventive concept on the basis of a principle that an inventor can properly define the concept of a term to explain his or her own invention in the best ways.

The present invention provides a bismuth molybdate-based composite oxide catalyst for preparing 1,3-butadiene, the catalyst having a microporous zeolite coating layer on the surface thereof.

In general, a naphtha cracking process, a direct dehydrogenation process of n-butene, and an oxidative dehydrogenation process of n-butene are known as a method of preparing 1,3-butadiene; and among these, the oxidative dehydrogenation process of n-butene is very advantageous thermodynamically because stable water is produced as a product, and it is exothermic contrary to the direct dehydrogenation so that 1,3-butadiene can be obtained with high yield even at a low temperature compared with the direct dehydrogenation. Therefore, the oxidative dehydrogenation process of n-butene is being recognized as an effective process.

However, as aforementioned, the oxidative dehydrogenation of n-butene is a reaction in which 1,3-butadiene and water are produced by the reaction of n-butene and oxygen, and thus has shortcomings that various side-reactions such as complete oxidation may occur because oxygen is used as a reactant, despite various advantages as a commercial process. Therefore, for an efficient process, it is necessary to develop a catalyst having high selectivity for 1,3-butadiene while maintaining high activity by allowing oxidative ability to be properly controlled.

A bismuth molybdate-based composite oxide catalyst according to an embodiment of the present invention is derived to supplement the aforementioned shortcomings, and characterized by including a bismuth molybdate-based composite oxide expressed by Formula 1 below; and a microporous zeolite coating layer formed on the surface of the bismuth molybdate-based composite oxide.

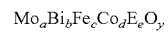  [Formula 1]

where, E is at least one selected from the group consisting of nickel, sodium, potassium, rubidium, and cesium; the a, b, c, d and e each is 0.001 to 1; and the y is a value determined to adjust a valence by other element.

In Formula 1, it may be preferable that E is at least one selected from the group consisting of cesium and potassium.

Preferably, the bismuth molybdate-based composite oxide catalyst for preparing 1,3-butadiene according to an embodiment of the present invention has such a structure that a microporous zeolite coating layer is formed on the surface of the bismuth molybdate-based composite oxide core.

Preferably, the zeolite is zeolite including silicon and aluminum together, aluminum-based zeolite, or silicon (Si)-based zeolite. Specifically, the zeolite may be silicon-based zeolite, such as zeolite consisting of only $SiO_2$. When the zeolite is silicon-based zeolite, products can be obtained with better yield than other types of zeolite.

Preferably, the zeolite coating layer has micropores with a diameter of 0.2 to 1.5 nm, and has a thickness of 50 to 1,000 nm. When the thickness of the zeolite coating layer is less than 50 nm, the coating layer may not sufficiently cover the bismuth molybdate-based composite oxide core, and thus solid organic by-products produced in the process of preparing 1,3-butadiene using the zeolite coating layer may easily escape from the coating layer, thereby causing an increase in formation of the solid organic by-products. On the other hand, when the thickness of the coating layer is greater than 1,000 nm, it may not be easy for reactants to access to the surface of the bismuth molybdate-based composite oxide core where active sites exist, during the process of preparing 1,3-butadiene using the zeolite coating layer, thereby resulting in a decrease in a conversion rate of reactants and thus reducing catalytic activity.

Catalysis of the bismuth molybdate-based composite oxide catalyst having a zeolite coating layer according to an embodiment of the present invention is schematically illustrated in FIG. 1.

Hereinafter, the catalysis will be described in detail with reference to FIG. 1.

A zeolite coating layer 10 according to an embodiment of the present invention includes micropores, which enables only reactants (1-butene and oxygen) 1 having a size less than the pores and gaseous products (light) 3 including 1,3-butadiene to selectively pass therethrough, thus increasing selectivity for target products. Furthermore, solid organic by-products 2 among products produced by dehydrogenation of butene have a particle size greater than micropores in the zeolite coating layer, so that they cannot escape the zeolite coating layer. Thus, the solid organic by-products are separated from the target products and adhere to the surface of the core (the surface of the bismuth molybdate-based composite oxide), and the solid organic by-products adhered to the surface are discharged in the form of gaseous $CO_x$ compounds by continuously supplied oxygen. Accordingly, the present invention can overcome limitations such as a blockade of pipe line caused by solid organic by-products which are produced in conventional processes of preparing 1,3-butadiene, and facilitate a purification process of products through simplifying products as a gas phase.

Also, the present invention provides a method of preparing a bismuth molybdate-based composite oxide catalyst having a microporous zeolite coating layer on the surface thereof.

The method of preparing a bismuth molybdate-based composite oxide catalyst having a zeolite coating layer according to the present invention is characterized by including: preparing a bismuth molybdate-based composite oxide expressed by Formula 1 (step 1); dipping the prepared bismuth molybdate-based composite oxide into a zeolite seed solution and leaving the bismuth molybdate-based composite oxide as it is, and then drying and firing the bismuth molybdate-based composite oxide to form zeolite seeds on the surface of the bismuth molybdate-based composite oxide (step 2); and impregnating, into a zeolite synthesizing solution, the bismuth molybdate-based composite oxide with the zeolite seeds formed, and then drying the bismuth molybdate-based composite oxide (step 3).

Figure 2:
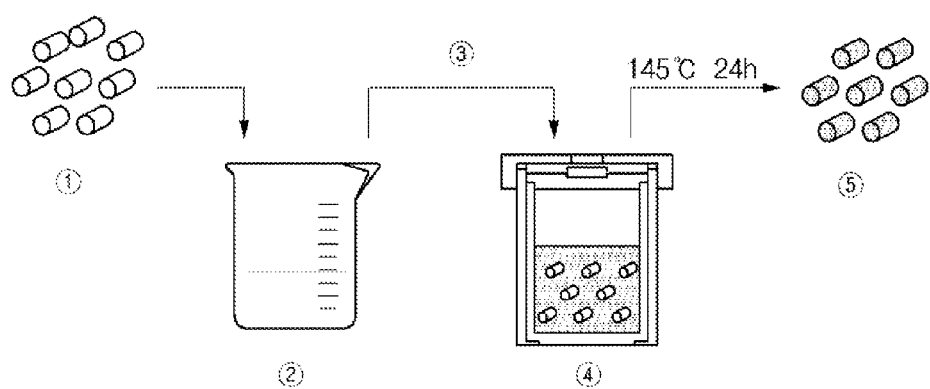
FIG. 2 schematically illustrates a process of preparing a bismuth molybdate-based composite oxide catalyst having a zeolite coating layer according to an embodiment of the present invention.

Hereinafter, the present invention will be described in more detail with reference to FIG. 2.

The step 1 is to prepare a bismuth molybdate-based composite oxide ① which is a core material of a catalyst for preparing 1,3-butadiene, the catalyst having a zeolite coating layer, wherein the bismuth molybdate-based composite oxide may be in the form of a pellet.

The bismuth molybdate-based composite oxide according to an embodiment of the present invention may be prepared by the steps of:

1) preparing a first solution including a bismuth-containing precursor; an iron-containing precursor; a cobalt-containing precursor; and precursor(s) containing at least one metal selected from the group consisting of nickel, sodium, potassium, rubidium and cesium;

2) adding the first solution to a second solution in which a molybdenum-containing precursor is dissolved, and then mixing the first and second solutions to induce a reaction; and 3) drying, forming and firing the mixed solution after the reaction.

Each metal-containing precursor used in the bismuth molybdate-based composite oxide in step 1) is not limited particularly, but any metal-containing precursor ordinarily used in the art may be used as the metal-containing precursor.

Specifically, the nickel-, sodium-, potassium-, rubidium-, and cesium-containing precursors may be, for example but are not particularly limited to, ammonium, carbonate, nitrate, acetate or oxide of the each metal. The bismuth-containing precursor may be bismuth nitrate, and the molybdenum-containing precursor may be ammonium molybdate.

The step 1) includes preparing a first solution by mixing each metal-containing precursor material in a solvent, in order to mix metallic elements included in the bismuth molybdate-based composite oxide. The solvent may be, but is not limited to, distilled water. In this case, in order to increase solubility of the bismuth-containing precursor, the first solution may be prepared by adding a strong acid to the solvent additionally or by separately dissolving the bismuth-containing precursor in a solvent including a strong acid and then adding the separately dissolved solution to a solution in which the other metal-containing precursors are mixed. The strong acid may be, but is not limited to, nitric acid.

Step 2) includes dissolving the molybdenum-containing precursor in a solvent to prepare a second solution, then adding the first solution to the second solution, and mixing the first and second solutions to induce a reaction, in order to mix the molybdenum-containing precursor with the first solution. In this case, the reaction may be proceeded while the mixed solution is being agitated, and the agitation may be performed in a temperature range of 25 to 80° C. at an agitation rate of 100 to 800 rpm.

Step 3) includes drying, forming and firing products produced after the reaction to obtain a bismuth molybdate-based composite oxide. The firing may be performed for 1 to 24 hours at 400 to 600° C., preferably for 2 to 10 hours at 450 to 500° C.

The step 2) includes performing slip casting in order to form zeolite seeds on the bismuth molybdate-based composite oxide (①) prepared in the step 1)

The term "slip casting" used herein means a method of obtaining a solid molded article as a modified application of generally known slip casting, by which the solid molded article is obtained by mixing a seed material with water to prepare slurry, then dipping a mold into the slurry, leaving the mold as it is for a certain time and taking the mold out of the slurry, and thereafter drying and firing the mold. In this case, the mold is not removed.

The seed layer according to an embodiment of the present invention may be formed using the slip casting, and specifically, may be formed by dipping the bismuth molybdate-based composite oxide into the zeolite seed solution ② and leaving the bismuth molybdate-based composite oxide as it is for a certain time, then taking the bismuth molybdate-based composite oxide out of the zeolite seed solution, and thereafter drying and firing ③ the bismuth molybdate-based composite oxide.

The zeolite seed solution ② is slurry which is prepared by adding zeolite powder to distilled water, and may include 0.1 to 20 wt % of zeolite based on total weight of the seed solution.

The drying ③ may be performed by heat treatment for 5 to 100 hours at 90 to 200° C., and particularly for 10 to 30 hours at 110 to 150° C.

The firing ③ may be performed by heat treatment for 2 to 40 hours at 400 to 600° C., particularly at 400 to 500° C., and more particularly at 450 to 500° C.

The step 3) includes dipping the bismuth molybdate-based composite oxide having zeolite seeds into a zeolite synthesizing solution ④ to induce a hydrothermal reaction, then allowing the seeds to grow, and thereafter drying and firing the bismuth molybdate-based composite oxide, in order to prepare a bismuth molybdate-based composite oxide catalyst ⑤ having a microporous zeolite coating layer on the surface thereof.

The hydrothermal reaction may be proceeded for 3 to 200 hours at 100 to 200° C.

The drying may be performed by heat treatment for 1 to 24 hours at 110 to 200° C.

The zeolite synthesizing solution ④ includes a precursor for synthesis of zeolite, and may include a zeolite structure-directing agent (SDA) and a silica-containing precursor which forms a zeolite framework. The synthesizing solution may further include an aluminum-containing precursor.

The zeolite SDA may be, but is not limited to, generally in the type of quaternary ammonium, and the zeolite framework derived from the zeolite SDA may be, but is not limited to, MFI (ZSM-5) type, BEA (BETA) type, MOR (mordenite) type, LTA type, or the like.

The method of forming the zeolite coating layer in the steps 2) and 3) according to the present invention includes forming zeolite seeds on the surface of the bismuth molybdate: based composite oxide, and then allowing the seeds to grow to form the zeolite coating layer. Thus, the zeolite coating layer is homogeneously synthesized on the surface of a core layer without any separation between the bismuth molybdate-based composite oxide core and the zeolite coating layer.

Also, the present invention provides a method of preparing 1,3-butadiene using the bismuth molybdate-based composite oxide catalyst having a zeolite coating layer on the surface thereof.

The method of preparing 1,3-butadiene according to the present invention is characterized by including: filling a reactor with the bismuth molybdate-based composite oxide catalyst having a microporous zeolite coating layer as a fixed bed (step A); and performing oxidative dehydrogenation while continuously passing reactants containing C4 compounds including n-butene through a catalyst layer of the reactor filled with the catalyst (step B).

Preferably, the oxidative dehydrogenation may be performed at a reaction temperature of 250 to 450° C. and at a space velocity of 50 to 5,000 $h^{-1}$ based on the n-butene.

Hereinafter, the following Example and Experimental Examples will be provided to describe the present invention in more detail. However, the following Example and Experimental Examples are intended to exemplify the present invention, and thus the scope of the present invention is not limited thereto.

EXAMPLE

1) Preparation of a Pellet-Type Bismuth Molybdate-Based Composite Oxide Core

A first solution was prepared in such a way that bismuth nitrate pentahydrate, iron nitrate nonahydrate ($Fe(NO_3)_3.9(H_2O)$), cobalt nitrate hexahydrate ($Co(NO_3)_2.6(H_2O)$), potassium nitrate ($KNO_3$), and cesium nitrate ($CsNO_3$) was added to distilled water and then mixed. In this case, the bismuth nitrate pentahydrate as a bismuth-containing precursor was added after being dissolved in distilled water mixed with nitric acid. Herein, each of the metal-containing precursor materials was used such that a molar ratio of molybdenum (Mo), bismuth (Bi), iron (Fe), cobalt (Co), cesium (Cs), and potassium (K) is adjusted to be 12:1:1:8:0.5:0.01. Subsequently, the first solution was added to a second solution which was prepared by dissolving ammonium molybdate tetrahydrate (($NH_4)_6(Mo_7O_{24}).4(H_2O)$) in distilled water, and then the added solution was mixed and agitated. Thereafter, products were dried and formed, and then fired at 450° C. to obtain a pellet-type bismuth molybdate-based composite oxide core.

2) Preparation of a Bismuth Molybdate-Based Composite Oxide Catalyst Having a Zeolite Coating Layer A zeolite coating layer was formed on the surface of the pellet-type bismuth molybdate-based composite oxide core prepared in Example 1). The coating layer was formed by forming a zeolite seed layer on the surface of the composite oxide core using a slip casting method, then dipping the composite oxide core having the seed layer into a zeolite synthesizing solution to induce hydrothermal synthesis, and thereafter drying and firing the composite oxide core.

The pellet-type bismuth molybdate-based composite oxide core was dipped into a zeolite seed solution (zeolite slurry, a solution containing 2 wt % of zeolite) and then left as it was for a certain time. Subsequently, the pellet-type bismuth molybdate-based composite oxide core was taken out and firmly hardened by being dried and fired. Thereafter, the composite oxide core having the seed layer was dipped into the zeolite synthesizing solution, and hydrothermally synthesized for 24 hours at 145° C. to obtain a pellet-type bismuth molybdate-based composite oxide catalyst having a zeolite coating layer. A process of forming a zeolite coating layer was schematically illustrated in FIG. 2.

Comparative Example

A pellet-type bismuth molybdate-based composite oxide catalyst without a zeolite coating layer was prepared.

A first solution was prepared in such a way that bismuth nitrate pentahydrate, iron nitrate nonahydrate ($Fe(NO_3)_3.9(H_2O)$), cobalt nitrate hexahydrate ($Co(NO_3)_2.6(H_2O)$), potassium nitrate ($KNO_3$), and cesium nitrate ($CsNO_3$) was added to distilled water and then mixed. In this case, the bismuth nitrate pentahydrate as a bismuth-containing precursor was added after being dissolved in distilled water mixed with nitric acid. Herein, each of the metal-containing precursor materials containing was used such that a molar ratio of molybdenum (Mo), bismuth (Bi), iron (Fe), cobalt (Co), cesium (Cs), and potassium (K) is adjusted to be 12:1:1:8:0.5:0.01. Subsequently, the first solution was added to a second solution which was prepared by dissolving ammonium molybdate tetrahydrate ($(NH_4)_6(Mo_7O_{24}).4(H_2O)$) in distilled water, and then the added solution was mixed and agitated. Thereafter, products were dried and formed, and then fired at 450° C. to obtain a pellet-type bismuth molybdate-based composite oxide catalyst.

Experimental Example 1: Morphology Analysis of Catalyst

For comparative analysis of morphologies of the bismuth molybdate-based composite oxide catalyst having a zeolite coating layer, which was prepared in the above Example, and the bismuth molybdate-based composite oxide catalyst without a zeolite coating layer, which was prepared in Comparative Example, surface morphologies and elementary compositions on the surface of the each catalyst were analyzed using scanning electron microscopy (SEM) and scanning electron microscopy & energy-dispersive X-ray spectroscopy (SEM-EDX). The results are shown in FIGS. 3 and 4.

Figure 3A:
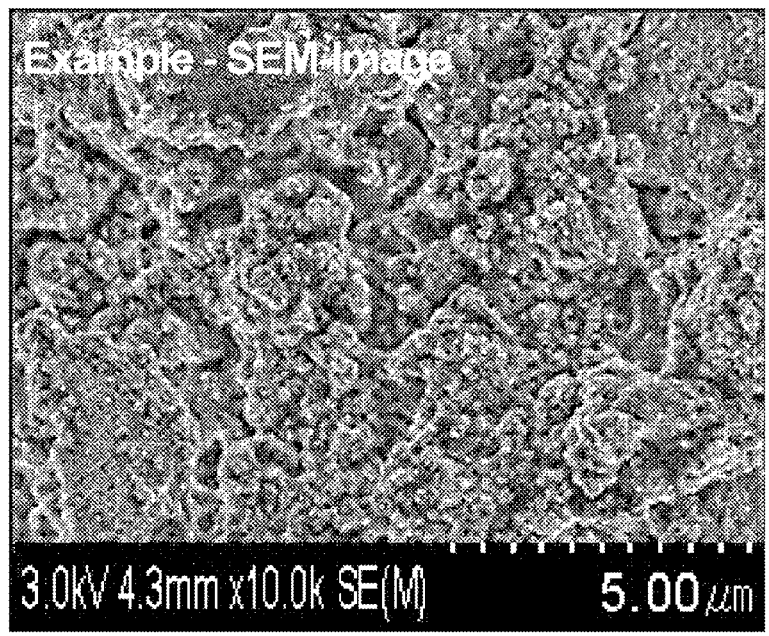
FIG. 3A is a scanning electron micrograph.
Figure 3B:
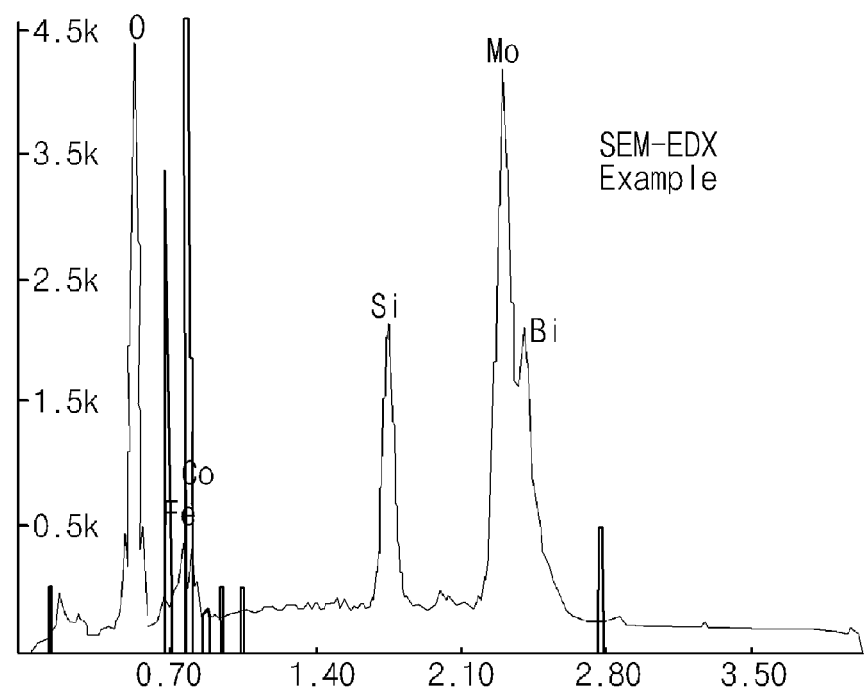
FIG. 3B is a graph showing an elementary composition on the surface of the catalyst analyzed using SEM-EDX.

FIG. 3 shows results obtained from morphology analysis of a molybdate-based composite oxide catalyst having a zeolite coating layer, which was prepared in Example, wherein FIG. 3A is a scanning electron micrograph, and FIG. 3B is an elementary composition on the surface of the catalyst analyzed using SEM-EDX.

Figure 4A:
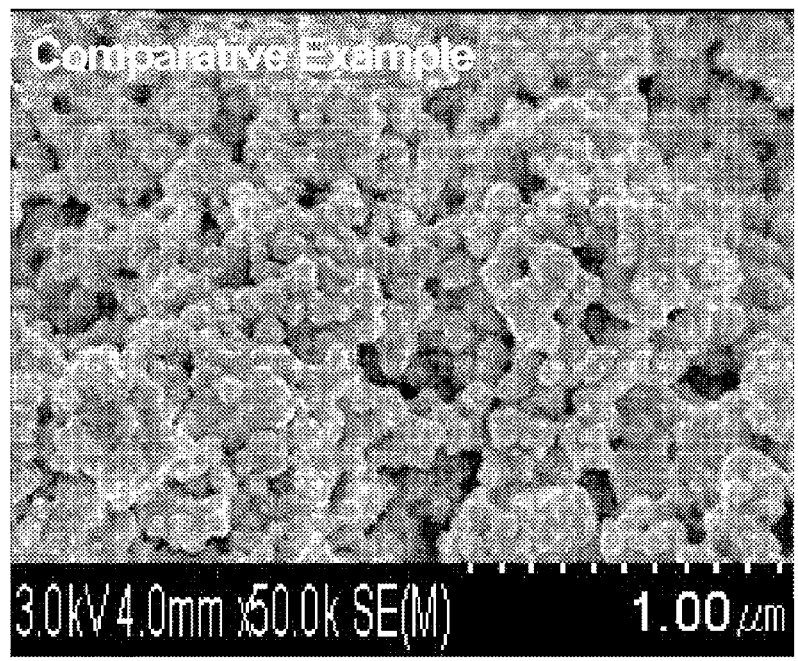
FIG. 4A is a scanning electron micrograph.
Figure 4B:
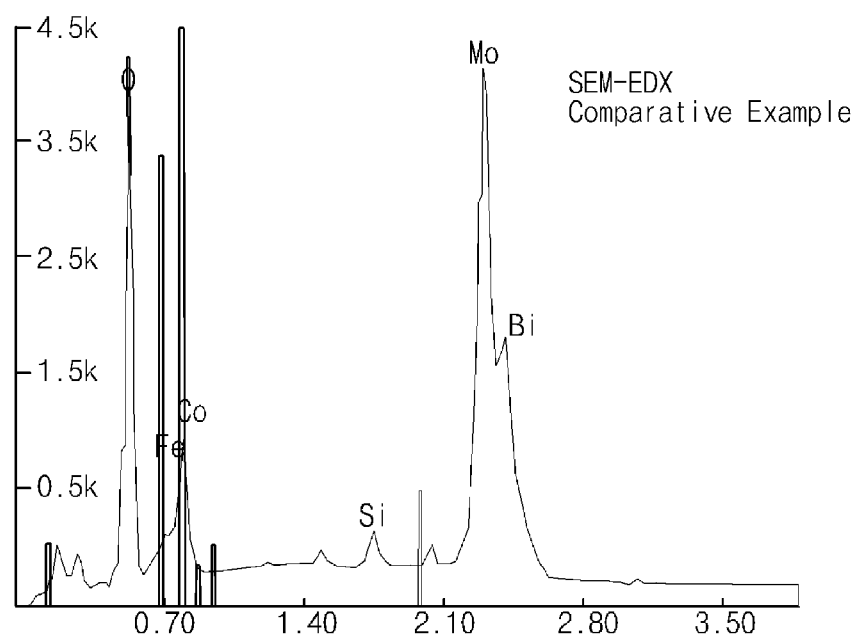
FIG. 4B is an elementary composition on the surface of the catalyst analyzed using SEM-EDX.

FIG. 4 shows results obtained from morphology analysis of a bismuth molybdate-based composite oxide catalyst without a zeolite coating layer, which was prepared in Comparative Example, wherein FIG. 4A is a scanning electron micrograph, and FIG. 4B is an elementary composition on the surface of the catalyst analyzed using SEM-EDX.

As shown in FIGS. 3 and 4, the bismuth molybdate-based composite oxide catalyst in Example (FIG. 3A) and the bismuth molybdate-based composite oxide catalyst in Comparative Example (FIG. 4A) showed different surface morphologies, and specifically, it was confirmed that the surface of the bismuth molybdate-based composite oxide catalyst in Example was covered with a zeolite crystal.

This was also verified from the result of SEM-EDX. Specifically, from the results of SEM-EDX, comparing the elementary compositions on the surface of the bismuth molybdate-based composite oxide catalysts in Example (FIG. 3B) and Comparative Example (FIG. 4B), it could be confirmed that a proportion of silicon element on the surface of the bismuth molybdate-based composite oxide catalyst in Example significantly increased. This result means that a zeolite coating layer is formed on the surface of the bismuth molybdate-based catalyst.

Experimental Example 2: Analysis of Activity of Catalyst

For comparative analysis of activities of the bismuth molybdate-based composite oxide catalyst having a zeolite coating layer, which was prepared in the above-mentioned Example, and each of the catalysts prepared in Comparative Examples 1 and 2, a conversion rate of 1-butene (X), selectivity for 1,3-butadiene (S-BD), selectivity for solid organic by-products (S-heavy), selectivity for $CO_x$ (S—$CO_x$), and hot spot temperature (HST) were measured by the following method. The results are shown in Table 1 below.

1-butene and oxygen were used as reactants, and additionally, nitrogen and steam were introduced together. A metallic tubular reactor was used as a reactor. The ratio of reactants and gas hourly space velocity (GHSV) were set on the basis of 1-butene. The ratio of butene, oxygen, steam, and nitrogen was set to be 1:0.75:6:10, and the GHSV was adjusted to be constant 50 $h^{-1}$ or 75 $h^{-1}$ depending on test conditions on the basis of 1-butene. The volume of a catalyst layer which contacts reactants was fixed to be 200 cc, and a reaction apparatus was designed such that water was injected to a vaporizer, vaporized into steam at 340° C., and the steam was mixed with 1-butene and oxygen which were other reactants and introduced into the reactor. Reaction temperature was maintained to be 300° C., 320° C., and 340° C., and products after reaction were analyzed using gas chromatography. The products include solid organic by-products such as trans-2-butene and cis-2-butene, in addition to 1,3-butadiene as a target product. The conversion rate of 1-butene (X), selectivity for 1,3-butadiene (S-BD), selectivity for solid organic by-products (S-heavy), and selectivity for $CO_x$ (S—$CO_x$) were calculated by Equations 1 to 4 below, respectively.

$$C_R = \frac{M_{R(B)}}{M_{P(B)}} \times 100 \quad \text{[Equation 1]}$$

where, $C_R$ is conversion rate of 1-butene (%); $M_R$ is moles of reacted 1-butene; and $M_P$ is moles of provided 1-butene.

$$S_{BD} = \frac{M_{P(BD)}}{M_{R(B)}} \times 100 \quad \text{[Equation 2]}$$

where, $S_{BD}$ is selectivity for 1,3-butadiene (%); $M_{P(BD)}$ is moles of produced 1,3-butadiene; and $M_{R(B)}$ is moles of reacted 1-butene.

$$S_h = \frac{M_{R(SO)}}{M_{R(B)}} \times 100 \quad \text{[Equation 3]}$$

where, $S_h$ is selectivity for solid organic by-products (%); $M_{R(SO)}$ is moles of reacted solid organic by-products; and $M_{R(B)}$ is moles of reacted 1-butene.

$$S_{CO_x} = \frac{M_{P(S)}}{M_{R(B)}} \times 100 \quad \text{[Equation 4]}$$

where, $S_{CO_x}$ is selectivity for $CO_x$ (%); $M_{P(S)}$ is moles of produced $CO_x$; and $M_{R(B)}$ is moles of reacted 1-butene.

TABLE 1

| Item | Conversion rate (%) | S-BD (%) | S-heavy (%) | S—$CO_x$ (%) | HST (° C.) |
|---|---|---|---|---|---|
| Example | 97.7 | 92.28 | 0.42 | 1.89 | 381.0 |
| Comparative Example | 97.96 | 92.90 | 1.42 | 1.78 | 389.3 |

As shown in Table 1, the bismuth molybdate-based composite oxide catalyst in Example according to the present invention showed a conversion rate of 1-butene and selectivity for 1,3-butadiene with an equivalent level as compared with the bismuth molybdate-based composite oxide catalyst in Comparative Example, and selectivity for solid organic by-products was reduced.

Specifically, the bismuth molybdate-based composite oxide catalyst having a zeolite coating layer according to the present invention (Example) showed a conversion rate of a reactant (conversion rate of 1-butene) and selectivity for a target product (selectivity for 1,3-butadiene) with an equivalent level as compared with the bismuth molybdate-based composite oxide catalyst without a zeolite coating layer (Comparative Example), and selectivity for by-products (selectivity for solid organic by-products) was reduced to 30% level. This result means that solid organic by-products were selectively separated by a zeolite coating layer according to the present invention.

Also, the bismuth molybdate-based composite oxide catalyst having a zeolite coating layer (Example) showed a slightly increased selectivity for $CO_x$ as compared with the bismuth molybdate-based composite oxide catalyst without a zeolite coating layer (Comparative Example), and this result implies that some of the solid organic by-products were converted into $CO_x$ by a reaction with oxygen contained in reactants.

While this invention has been particularly shown and described with reference to preferred embodiments thereof and drawings, it will be understood by those skilled in the art that various changes in form and details may be made therein without departing from the spirit and scope of the invention as defined by the appended claims.

The invention claimed is:

1. A bismuth molybdate-based composite oxide catalyst for preparing 1,3-butadiene, comprising:
a bismuth molybdate-based composite oxide having a molar ratio of metal components of Formula 1:

$$Mo_aBi_bFe_cCo_dE_eO_y \qquad \text{[Formula 1]}$$

wherein:
E is at least one selected from the group consisting of nickel, sodium, potassium, rubidium, and cesium;
the a, b, c, d and e each is a number from 0.001 to 1; and
the y is a value determined to adjust a valence by other element; and
a zeolite coating layer having micropores and formed on the surface of the bismuth molybdate-based composite oxide,
wherein the micropores have a diameter of 0.2 to 1.5 nm and the zeolite coating layer has a thickness of 50 to 1,000 nm.

2. The bismuth molybdate-based composite oxide catalyst according to claim 1, wherein the E is at least one selected from the group consisting of cesium and potassium.

3. The bismuth molybdate-based composite oxide catalyst according to claim 1, wherein the zeolite is silicon-based zeolite.

4. The bismuth molybdate-based composite oxide catalyst according to claim 1, wherein the bismuth molybdate-based composite oxide catalyst is in the form of a pellet.

5. A method of preparing a bismuth molybdate-based composite oxide catalyst for preparing 1,3-butadiene, the bismuth molybdate-based composite oxide catalyst including a zeolite coating layer having micropores on the surface thereof, the method comprising:

1) preparing a bismuth molybdate-based composite oxide expressed by Formula 1:

$$Mo_aBi_bFe_cCo_dE_eO_y \qquad \text{[Formula 1]}$$

wherein:
E is at least one selected from the group consisting of nickel, sodium, potassium, rubidium, and cesium;
the a, b, c, d and e each is 0.001 to 1; and
the y is a value determined to adjust a valence by other element;

2) pouring a zeolite seed solution over the prepared bismuth molybdate-based composite oxide and leaving the bismuth molybdate-based composite oxide as it is, then drying and firing the bismuth molybdate-based composite oxide to form zeolite seeds on the surface of the bismuth molybdate-based composite oxide; and 3) impregnating, into a zeolite synthesizing solution, the bismuth molybdate-based composite oxide with the zeolite seeds formed, to allow the seeds to grow, and then drying the bismuth molybdate-based composite oxide,
wherein the micropores have a diameter of 0.2 to 1.5 nm and the zeolite coating layer is formed to have a thickness of 50 to 1,000 nm.

6. The method according to claim 5, wherein the bismuth molybdate-based composite oxide in step 1) is prepared by:
preparing a first solution including a bismuth-containing precursor; an iron-containing precursor; a cobalt-containing precursor; and precursor(s) containing at least one metal selected from the group consisting of nickel, sodium, potassium, rubidium and cesium;
adding the first solution to a second solution in which a molybdenum-containing precursor is dissolved, and then mixing the first and second solutions to induce a reaction; and
drying, forming and firing the mixed solution after the reaction.

7. The method according to claim 5, wherein the zeolite is silicon-based zeolite.

8. The method according to claim 5, wherein the drying in step 2) is performed by heat treatment for 5 to 100 hours at 90 to 200° C.

9. The method according to claim 5, wherein the firing in step 2) is performed by heat treatment for 2 to 40 hours at 400 to 600° C.

10. The method according to claim 5, wherein the drying in step 3) is performed by heat treatment for 1 to 24 hours at 110 to 200° C.

11. The method according to claim 5, wherein the bismuth molybdate-based composite oxide catalyst is in the form of a pellet.

12. A method of preparing 1,3-butadiene, the method comprising:
filling a reactor with the bismuth molybdate-based composite oxide catalyst for preparing 1,3-butadiene according to claim 1 as a fixed bed; and
performing oxidative dehydrogenation while continuously passing reactants containing C4 compounds including n-butene through a layer of the bismuth molybdate-based composite oxide catalyst of the reactor filled with the bismuth molybdate-based composite oxide catalyst.

13. The method according to claim 12, wherein the oxidative dehydrogenation is performed at a reaction temperature of 250 to 450° C. and at a space velocity of 50 to 5,000 $h^{-1}$ based on the n-butene.

* * * * *